Aug. 29, 1950 J. DE VINK Plant Pat. 976
ROSE PLANT
Filed Oct. 24, 1949
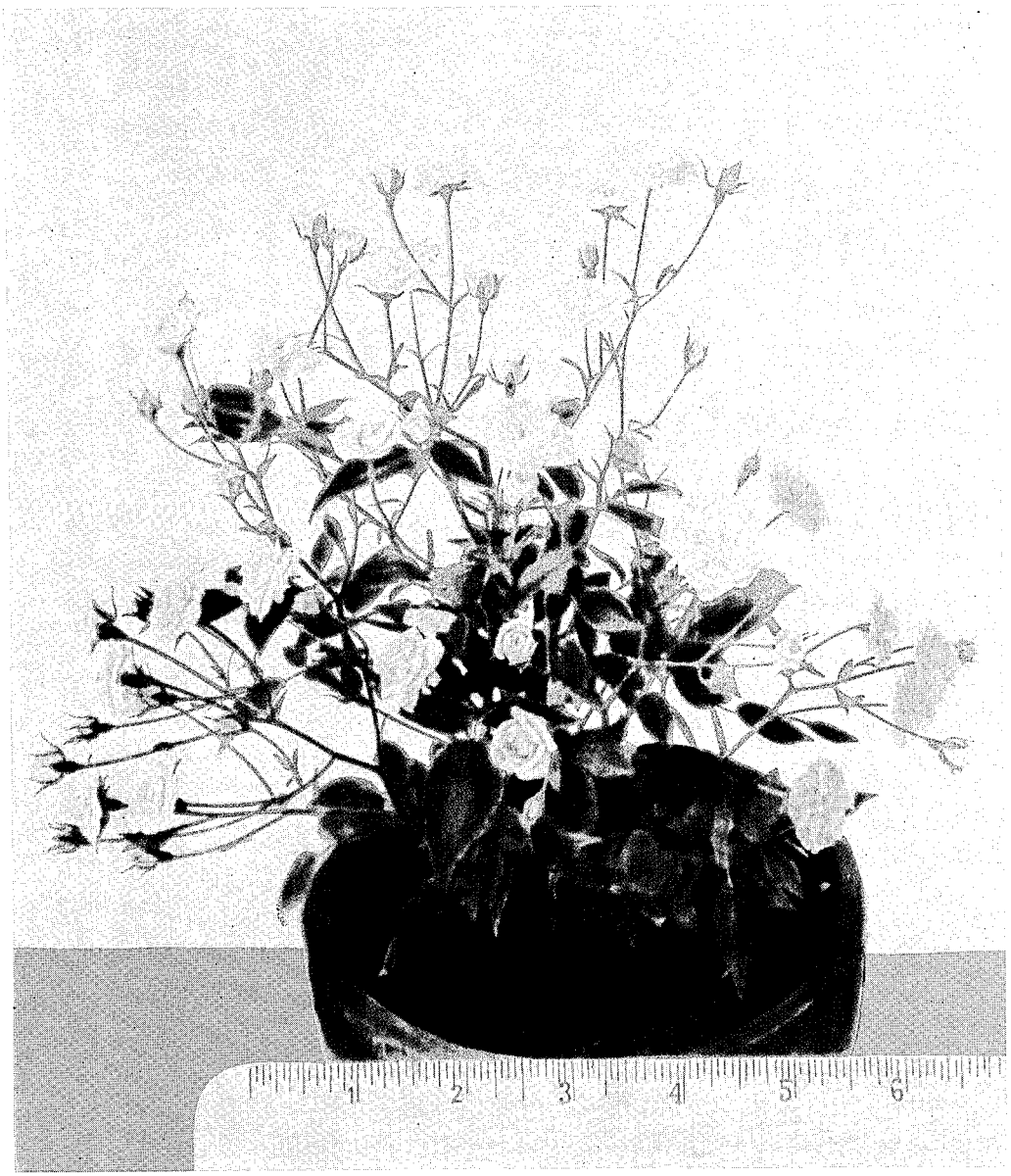
Inventor
John de Vink
By Robb & Robb
attorneys Patented Aug. 29, 1950 Plant Pat. 976

UNITED STATES PATENT OFFICE

976

ROSE PLANT

John de Vink, Boskoop, Netherlands, assignor to The Conard-Pyle Company, West Grove, Pa., a corporation of Pennsylvania Application October 24, 1949, Serial No. 123,253

1 Claim. (Cl. 47—61)

The present invention relates to a new and distinct variety of rose plant of the miniature class, the novel characteristics of which, when comparison is made with other known roses of this class, reside in the fact that the plant is more erect in growth habit; more floriferous—blooming in candelabra-like sprays; and bears flowers of a new shade of pink, deeper and richer than any previously known variety of pink miniature rose.

This new variety is like neither one of its parents. The seed parent, in open bloom, is far more globular; while the new variety is globular in the bud form or stage of development, it gradually opens to a rather flat form. But it is very distinctive in habit of growth in the fact that it is quite candelabra-like, as hereinbefore stated. The blooms are borne on the tips of stems that are erect and curving like a spray of a fountain, whereas "Tom Thumb," on the other hand, is squatty and irregular in the manner in which the clusters are borne.

Asexual reproduction of this new variety shows the foregoing characteristics come true to form and are established.

The drawing illustrates a specimen of the miniature plant of this invention as set in a pot and shows the foliage and blooms in various stages of development from buds to fully open flowers, particularly depicting the way the flowers bloom in a spray. At the bottom of the illustration is shown an inch scale for comparison as to actual size.

This new variety was asexually reproduced at West Grove, Pennsylvania.

The following is a detailed description of the new variety, reference to color being in accordance with Ridgway's Color Standards and Nomenclature and in accordance with ordinary dictionary meaning:

Type: Hardy; dwarf; greenhouse; outdoor; seedling; for cut flowers and garden decoration.

Class: Miniature.

Breeding: Seedling.

*Seed parent.*—"Mlle. Cecile Brunner". (Unpatented)

*Pollen parent.*—"Tom Thumb" (Pl. Pat. No. 169).

Propagation: Holds its distinguishing characteristics through succeeding propagations by cuttings.

Locality where grown: West Grove, Pennsylvania.

Flowers borne: Several to many to stem; in irregular cluster; on strong long (for a miniature) stems.

Quantity of bloom: Abundant in greenhouse.

Continuity: Intermittent to continuous.

Fragrance: Very slight.

Bud:

*Peduncle.*—Long for a miniature; erect; stiff; slender; almost smooth; few very small prickles. Color—Parrot Green, Plate VI.

*Before calyx breaks.*—Size—small. Form—pointed; ovoid; with foliaceous appendages on the surface of the bud; with slender little cut foliaceous parts extending beyond the tip of the bud equal to one-fourth or more of its length.

*As calyx breaks.*—Color—Spinel Red, Plate XXVI.

*As bud first opens.*—Size—very small. Form—medium length for a miniature; globular-cup-shape. Color—outside: Spinel Pink, Plate XXVI, to Spinel Red, Plate XXVI; inside: Deep Rose Pink, Plate XII, to Rose Color, Plate XII.

*Opening.*—Opens up well.

Bloom:

*Size, when fully open.*—Very small; ¾ inch to 1 inch.

*Pentalage.*—Double to very double; from 25 to 30 petals arranged regularly.

*Form.*—Very cupped at first; petals remaining at first cupped; becoming later, at maturity, rather flat, slightly rolled outward.

Petals: Medium thin; with inside and outside silky.

*Shape.*—Outer—obovate, with apex rounded. Intermediate—oval, with apex rounded. Inner—oval, with apex rounded.

*Color.*—Colors may be modified by being penciled and shaded with Tyrian Pink, Plate XII, and traces of white.

This description of a newly opened flower was made from a rose grown in a greenhouse in the month of April at West Grove, Pennsylvania:

*Color.—Outer petal*—outside surface: Pale Green Yellow, Plate V, at base; shading to Pinkish Vinaceous, Plate XXVII, and to Spinel Red, Plate XXVI, at outer edge of petal; inner surface: Pale Green Yellow, Plate V, at base; shading to Pinkish Vinaceous, Plate XXVII, at edges. *Intermediate petal*—outside surface: white at base; Deep Rose Pink, Plate XII, or sometimes Rosolane Pink, Plate XXVI, over most of petal surface; inside surface: white at base; Deep Rose Pink, Plate XII, or light Rosolane Pink, Plate XXVI, over most of petal surface. *Inner petal*—outside surface: white at base; Deep Rose Pink, Plate XII, or Rose Pink, Plate XII, over most of petal surface, sometimes shading to Rosolane Pink, Plate XXVI; inside surface—white at base; Deep Rose Pink, Plate XII, or sometimes Rosolane Pink, Plate XXVI, over most of petal surface, occasionally with veinings of Rose Color, Plate XII.

This description was made from a rose that was open for three days in a greenhouse in April at West Grove, Pennsylvania (because the flower opens slowly, this is not a fully open flower):

*Color.—Outer petal*—outside surface: white to Light Viridine Green, Plate VI, at base; most of petal surface shading from Rosolane Pink, Plate XXVI, to Thulite Pink, Plate XXVI; or sometimes shading to Spinel Red, Plate XXVI, or Deep Rose Pink, Plate XII, occasionally touched with Rose Color, Plate XII; inside surface: white to pale Opaline Green, Plate VII, at base; most of petal surface shading from pale Rosolane Pink, Plate XXVI, to Rose Pink, Plate XII; sometimes shading from Pale Congo Pink, Plate XXVIII, to Light Congo Pink, Plate XXVIII. *Inner petal*—outside surface: white to light Opaline Green, Plate VII, at base; most of petal surface shading from Cameo Pink, Plate XXVI, occasionally with darker veinings of Deep Rose Pink, Plate XII, to dark Rosolane Pink, Plate XXVI, or sometimes shading to Rose Pink, Plate XII, or to Deep Rose Pink, Plate XII; inside surface: white at base; most of petal surface shading from light Rosolane Pink, Plate XXVI, to Pale Rosolane Purple, Plate XXVI, occasionally with tinges of Deep Rose Pink, Plate XII.

*General color effect.*—Newly opened flower—inside of flower—Cameo Pink, Plate XXVI, at edges shading to light Thulite Pink, Plate XXVI, and to light Spinel Pink, Plate XXVI, toward center; outside of flower—Spinel Pink, Plate XXVI, occasionally with shadings of Thulite Pink, Plate XXVI. Three days open—Rosolane Pink, Plate XXVI, at edges, shading to Light Rosolane Purple, Plate XXVI, at the center; or shading from Cameo Pink, Plate XXVI, at edges to Thulite Pink, Plate XXVI, and to Spinel Pink, Plate XXVI, at center.

*Behavior.*—Drop off cleanly; fades in hot weather; intense coloring in cold weather; wet weather will induce spottiness of color.

*Flower longevity.*—On bush in greenhouse, 14 days in April.

*Reproductive organs*

Stamens: Variable; medium to many; arranged regularly about pistils, sometimes mixed with petaloids.

Filaments: Most with anthers; medium length; pale yellow.

Anthers: All open at various times; medium size; yellow; occasionally an anther fused with a petaloid.

Pollen: None evident at time of description.

Pistils: Medium number.

Styles: Fairly even; very short; very thin; bunched.

Stigma: White to reddish.

Ovaries: All enclosed in calyx.

Hips: Very minute; ovoid; very smooth; walls thin, dry; brown.

Sepals: Permanent; long in comparison to flower size; spear-shaped.

Seeds: None found at time of description.

*Plant*

Foliage:

*Leaves.*—Usually compound of 5 or 7 leaflets; normally abundant; very small; moderately heavy; semiglossy.

*Leaflets.*—Shape—ovate with apex acute; base round to obtuse; margin serrate.

*Color.—Mature*—upper surface: Elm Green, Plate XVII; under surface: Light Elm Green, Plate XVII. *Young*—upper surface: Forest Green, Plate XVII; under surface: Light Elm Green, Plate XVII.

*Rachis.*—Heavy for the size of the leaf. Upper side: grooved; under side: sparsely thorny.

*Stipules.*—Medium length in proportion to the leaves; medium wide; with moderately long points; turning out at an angle of less than 45°.

*Disease.*—Resistant.

Growth:

*Habit.*—Dwarf; bushy; upright; much branched.

*Growth.*—Moderately vigorous.

*Canes.*—Moderately heavy for a miniature.

*Main stems.*—Green. *Thorns*—several; medium length for a miniature; very slightly hooked downward; with short oval base. *Prickles and hairs*—none.

*Branches.*—Green. *Thorns*—few; medium length for a miniature; slightly hooked downward; with short oval base. *Prickles and hairs*—none.

*New shoots.*—Yellowish green. *Thorns*—none observed. *Prickles and hairs*—none.

I claim:

A new and distinct variety of rose plant of the dwarf or miniature type, characterized as to novelty by its erectness; its floriferousness; the candelabra-like sprays of its flowers; and the new pink shade of the blooms, substantially as shown and described.

JOHN DE VINK.

No references cited.